(12) United States Patent
Chen et al.

(10) Patent No.: US 9,788,816 B2
(45) Date of Patent: Oct. 17, 2017

(54) FLUID WITHDRAWING, EXPELLING AND FILTERING APPARATUS

(71) Applicants: MACKAY MEMORIAL HOSPITAL, Taipei (TW); SHIN YAN SHENO PRECISION INDUSTRIAL CO., LTD., Taichung (TW)

(72) Inventors: Schu-Rern Chen, Taipei (TW); Chih-Ping Chen, Taipei (TW); Ching-Kuei Lin, Taichung (TW)

(73) Assignees: Mackay Memorial Hospital, Taipei (TW); Shin Yan Sheno Precision Industrial Co., Ltd., Taichung (TW)

( * ) Notice: Subject to any disclaimer, the term of this patent is extended or adjusted under 35 U.S.C. 154(b) by 96 days.

(21) Appl. No.: 14/862,925

(22) Filed: Sep. 23, 2015

(65) Prior Publication Data

US 2016/0091399 A1    Mar. 31, 2016

(30) Foreign Application Priority Data

Sep. 30, 2014   (TW) .............................. 103134083 A

(51) Int. Cl.
    *A61B 10/00* (2006.01)
    *A61M 5/31* (2006.01)

(52) U.S. Cl.
    CPC ....... *A61B 10/0048* (2013.01); *A61M 5/3145* (2013.01)

(58) Field of Classification Search
    CPC .......................... A61B 10/0048; A61M 5/3145
    USPC ...................................................... 73/863.23
    See application file for complete search history.

(56) References Cited

U.S. PATENT DOCUMENTS

| | | | | |
|---|---|---|---|---|
| 4,391,274 A | * | 7/1983 | Kagan | A61M 5/165 604/190 |
| 5,494,044 A | * | 2/1996 | Sundberg | A61B 10/0291 600/562 |
| 5,575,777 A | * | 11/1996 | Cover | A61M 25/0606 604/110 |
| 6,796,965 B2 | | 9/2004 | Dumaresq-Lucas et al. | |
| 2009/0205644 A1 | * | 8/2009 | Tanaka | A61K 9/007 128/200.24 |
| 2011/0224610 A1 | * | 9/2011 | Lum | A61M 5/38 604/125 |
| 2016/0317748 A1 | * | 11/2016 | Seymour | A61M 5/165 |

FOREIGN PATENT DOCUMENTS

DK    WO 9617550 A1 *  6/1996   ......... A61B 10/0084

* cited by examiner

*Primary Examiner* — Hezron E Williams
*Assistant Examiner* — Marrit Eyassu
(74) *Attorney, Agent, or Firm* — Muncy, Geissler, Olds & Lowe, P.C.

(57) ABSTRACT

A fluid withdrawing, expelling and filtering apparatus includes a fluid container including a first chamber, a second chamber, and, a first through hole and a second through hole respectively disposed in communication between the first chamber and the second chamber, a filter device movable between a first position and a second position to open or close the second through hole of the fluid container and including a filter element mating with the first through hole, and a fluid withdrawing and expelling operator operable to withdraw and expel a fluid through the first chamber of the fluid container.

4 Claims, 3 Drawing Sheets

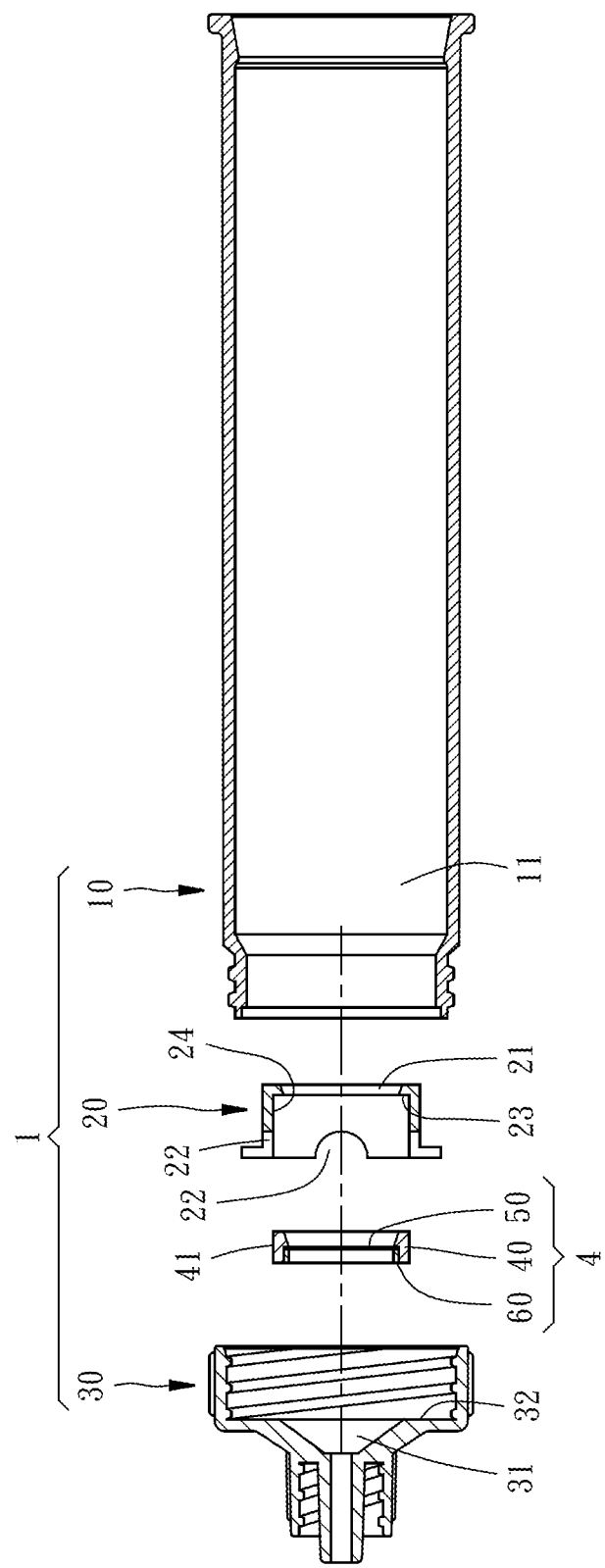

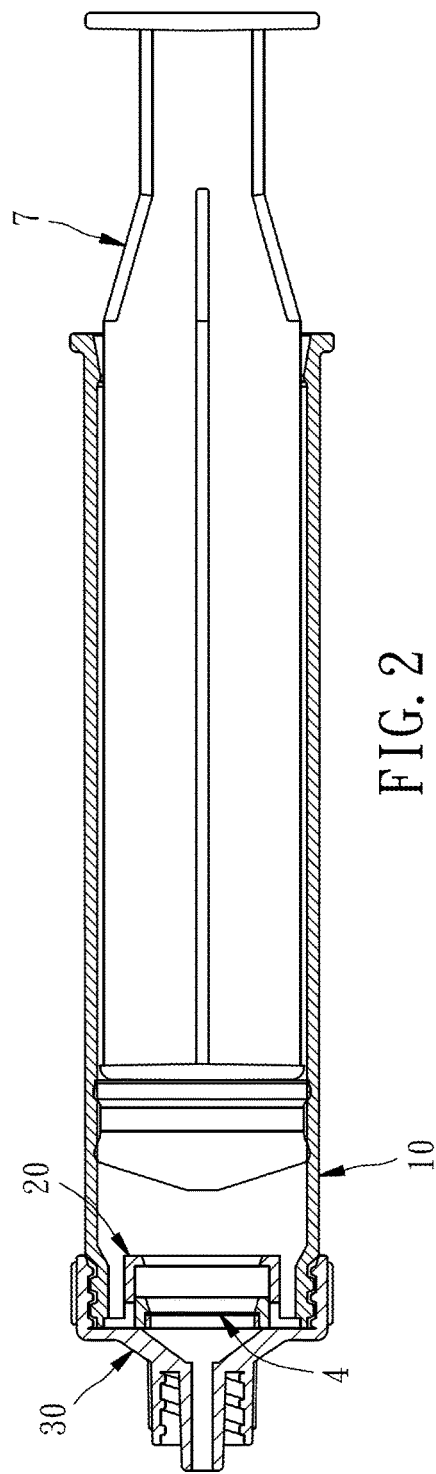
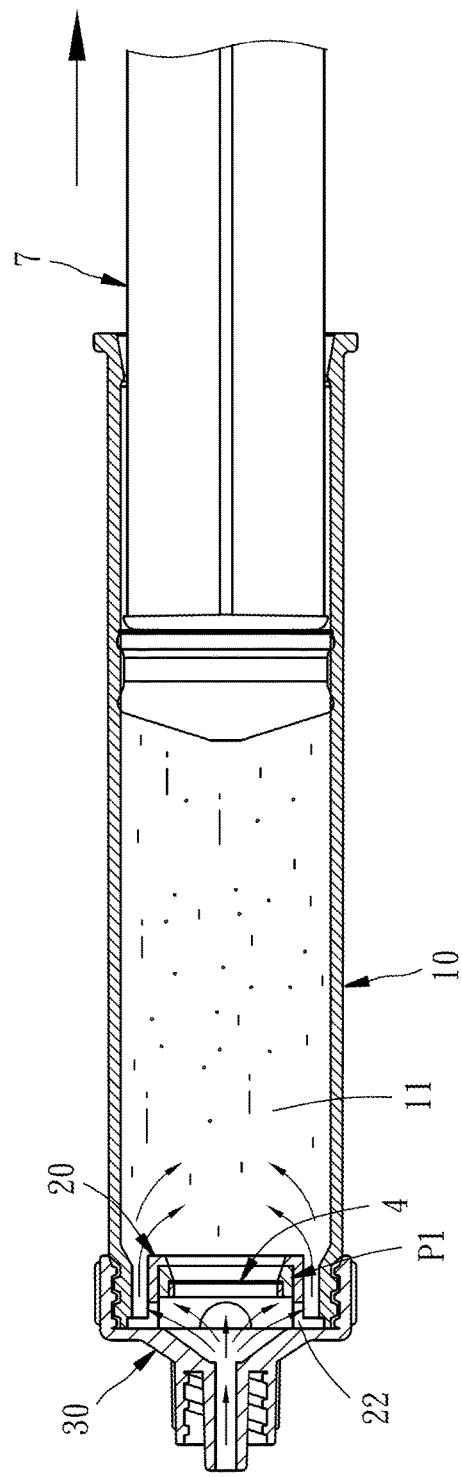

FLUID WITHDRAWING, EXPELLING AND FILTERING APPARATUS

BACKGROUND OF THE INVENTION

1. Field of the Invention

The present invention relates to medical equipment technology and more particularly, to a fluid withdrawing, expelling and filtering apparatus for sampling specimens from a fluid.

2. Description of the Related Art

U.S. Pat. No. 5,494,044 teaches a sampling device with a one-way valve including a cell filter for taking a sample of amniotic fluid. However, the filter provides no guide means, and a large amount of the cells in the intake flow of the amniotic fluid can be lost, resulting in an adequate amount of sampled cells.

U.S. Pat. No. 6,796,965 discloses a syringe with filter that has guide means mounted in the central axis and a filter element located on the circumference, thus, its reciprocating displacement in unstable and can be biased easily. Further, mounting the filter element in the circumference can cause formation of mixed flow, leading to a poor filtration effect.

Therefore, the prior art sampling devices are still not satisfactory in function, and have still room for improvement.

SUMMARY OF THE INVENTION

The present invention has been accomplished under the circumstances in view. It is the main object of the present invention to provide a fluid withdrawing, expelling and filtering apparatus, which facilitates quick and convenient operation, stabilizes reciprocating axial displacement, and achieves better effects in movement of a fluid through a filter element and collection of specimens from the fluid.

To achieve this and other objects of the present invention, a fluid withdrawing, expelling and filtering apparatus of the invention comprises a fluid container comprising a first chamber and a second chamber, and, a first through hole and a second through hole respectively disposed in communication between the first chamber and the second chamber, a filter device, which comprises a filter element facing toward the first through hole and is movable between a first position where the filter device opens the second through hole of the fluid container and a second position where the filter device closes the second through hole of the fluid container, and a fluid withdrawing and expelling operator operable to withdraw and expel a fluid through the first chamber of the fluid container.

The fluid withdrawing, expelling and filtering apparatus of the invention enables the filter device to be moved with a fluid in reversed directions to open or close the second through hole of the fluid container. Thus, the fluid withdrawing, expelling and filtering apparatus to withdraw a fluid rapidly through the second through hole of the fluid container, and then to expel the withdrawn fluid through the filter element of the filter device, leaving specimens deposited on the filter element.

Preferably, the first through hole is disposed relatively closer to the fluid withdrawing and expelling operator than the second through hole.

Preferably, the first through hole is located in the center of the fluid container.

Preferably, the second through hole is located in the periphery of the fluid container.

Preferably, the fluid container comprises a receptacle, and the first through hole is located in the receptacle.

Preferably, the fluid container comprises a receptacle, and the second through hole is located in the receptacle.

Preferably, the fluid container comprises a receptacle, and a first stop portion located in the receptacle.

Preferably, the fluid container comprises a front cap, and a second stop portion located in the front cap.

Preferably, the fluid container comprises a barrel, and a receptacle mounted in the barrel.

Preferably, the fluid container comprises a barrel, and a front cap mounted in the barrel.

Other advantages and features of the present invention will be fully understood by reference to the following specification in conjunction with the accompanying drawings, in which like reference signs denote like components of structure.

BRIEF DESCRIPTION OF THE DRAWINGS

FIG. 1 is an exploded view of a fluid withdrawing, expelling and filtering apparatus in accordance with the present invention.

FIG. 2 is a sectional assembly view of the fluid withdrawing, expelling and filtering apparatus in accordance with the present invention.

FIG. 3 is a schematic drawing illustrating an operation status of the fluid withdrawing, expelling and filtering apparatus in accordance with the present invention.

DETAILED DESCRIPTION OF THE INVENTION

Figure 4:
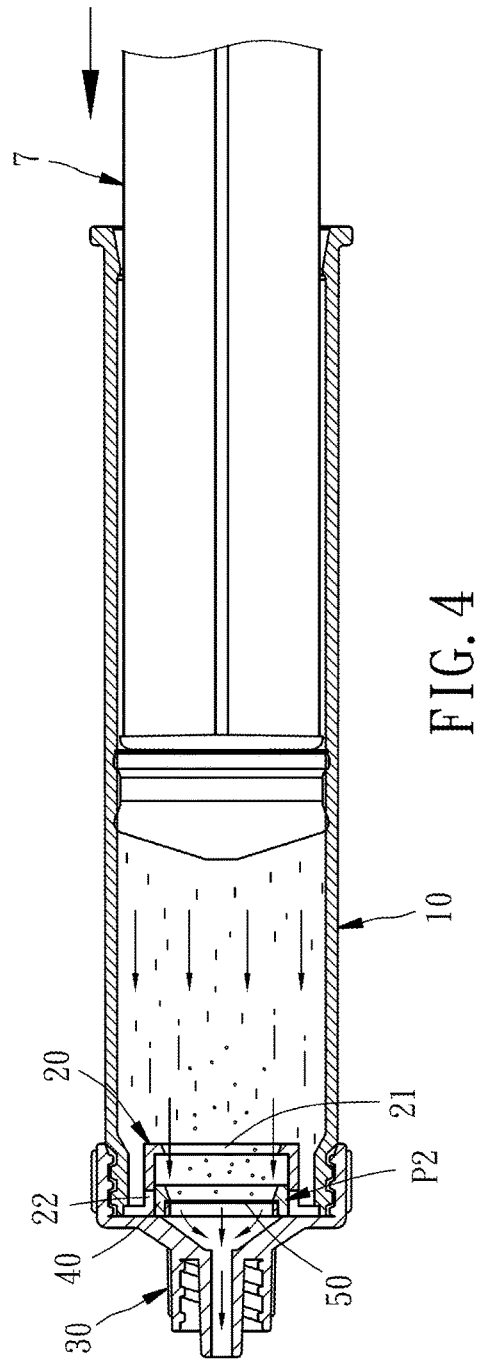
FIG. 4 is a schematic drawing illustrating another operation status of the fluid withdrawing, expelling and filtering apparatus in accordance with the present invention.

At first, it is to be noted that the directional terms of the adjectives of "inner", "outer", "upper" and "lower" are based on the directions in the annexed drawings.

Referring to FIGS. 1 and 2, a fluid withdrawing, expelling and filtering apparatus in accordance with the present invention is shown. The fluid sampling syringe comprises:

a barrel 10 comprising a first chamber 11 extending through opposing front and rear ends thereof;

a receptacle 20 mounted in the front open end of the barrel 10 comprising a first through hole 21 located in the center thereof in communication with the first chamber 11, a plurality of second through holes 22 spaced around the periphery thereof, and a first stop portion 23;

a front cap 30 fastened to, for example, threaded onto the front open end of the barrel 10 to hold down the receptacle 20 on the front end of the barrel 10, comprising a double open-ended second chamber 31 extending through opposing front and back sides thereof and disposed in communication with the second through holes 22 of the receptacle 20, and a second stop portion 32;

a filter device 4, comprising a carrier 40 movably accommodated in the straight hole-like inner perimeter of the receptacle 20, a filter element 50 mounted in the carrier 40 and facing toward the first through hole 21 of the receptacle 20, and a packing ring 60 mounted in the carrier 40 to secure the filter element 50 in position; and a fluid withdrawing and expelling operator 7 made in the form of, for example, a plunger airtightly inserted into the first chamber 11 of the barrel 10 and axially movable relative to the barrel 10 to draw a fluid into the first chamber 11, or to expel the fluid out of the first chamber 11.

Broadly speaking, the barrel 10, the receptacle 20 and the front cap 30 constitute a fluid container 1, i.e., the fluid container 1 comprises the first chamber 11, the second chamber 31, the first through hole 21 and the second through holes 22. The filter device 4 is movable between a first position P1 to open the second through holes 22 of the fluid container 1 and a second position P2 to close the second through holes 22 of the fluid container 1. In addition, the receptacle 20 is provided with a slidably-fitting inner periphery 24, and the filter device 4 is provided with a slidably-fitting outer periphery 41 slidably fitted with the slidably-fitting inner periphery 24 of the receptacle 20.

Further, the first through hole 21 of the receptacle 20 is disposed relatively closer to the fluid withdrawing and expelling operator 7 than the second through holes 22, constituting a preferred configuration.

The application of the present invention is outlined hereinafter.

Mount a needle not shown in the front cap 30 for inserting into the body of an object to take a fluid containing cells from the object, or directly insert the front cap 30 into a sampled fluid for taking cells from the sampled fluid. In operation, as shown in FIG. 3, pull the fluid withdrawing and expelling operator 7 backwardly relative to the barrel 10 to withdraw the aforesaid fluid through the second chamber 31 into the first chamber 11 of the barrel 10. At this time, the filter device 4 is forced by the intake flow of the fluid, causing separation of the carrier 40 of the filter device 4 from the receptacle 20 to open the second through holes 22, and the filter device 4 will then be stopped by the first stop portion 23 of the receptacle 20, and thus, the intake flow of fluid can go through the second through holes 22 of the receptacle 20 into the first chamber 11 of the barrel 10.

However, a part of the intake flow of fluid can go through the filter element 50 and the first through hole 21 into the first chamber 11 of the barrel 10.

Thereafter, as shown in FIG. 4, push the fluid withdrawing and expelling operator 7 forwards to move the fluid from the first chamber 11 of the barrel 10 toward the carrier 40 and filter element 50 of the filter device 4. At this time, the filter device 4 is moved forwards with the running fluid and stopped at the second stop portion 32 of the front cap 30, thereby closing the second through holes 22 of the receptacle 20. At this time, the fluid completely goes through the first through hole 21 and the filter element 50 of the filter device 4 into the second chamber 31 of the front cap 30, leaving the desired cells deposited on the filter element 50. Thus, the invention achieves optimal sampling.

Figure 5:
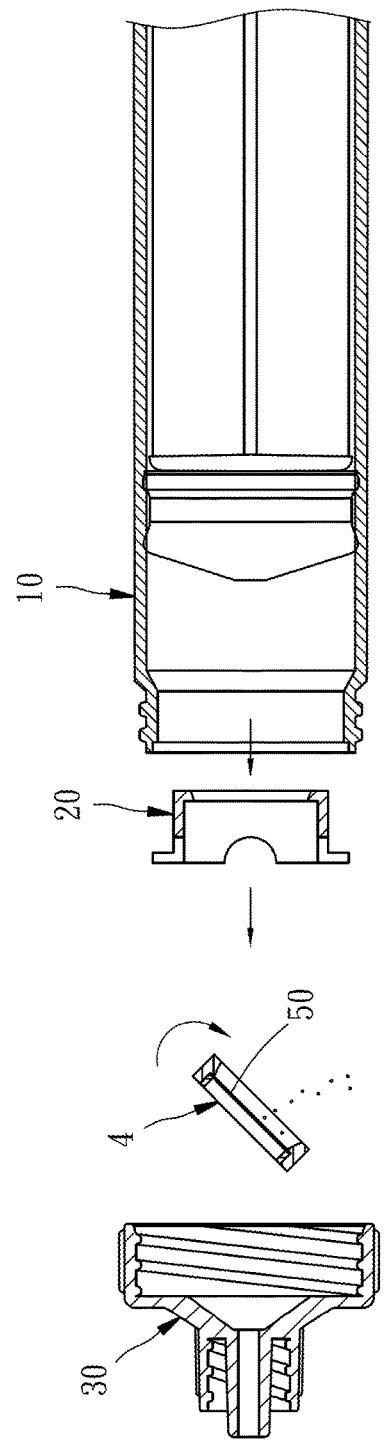
FIG. 5 is a schematic drawing illustrating still another operation status of the fluid withdrawing, expelling and filtering apparatus in accordance with the present invention.

As illustrated in FIG. 5, remove the front cap 30 from the barrel 10, and then remove the receptacle 20 from the barrel 10, and then remove the filter device 4 from the receptacle 20, and thus, the cells can be flushed from the filter element 50 of the filter device 4 by means of a culturing medium.

Further, various modifications and enhancements can be made without departing from the spirit and scope of the invention.

For example, except the design of making the barrel 10 in the form of a syringe barrel to fit the fluid withdrawing and expelling operator 7, the barrel 10 can be made for detachably attaching to the syringe barrel of a medical syringe.

In the aforesaid embodiment, the fluid container 1 is composed of the barrel 10, the receptacle 20 and the front cap 30. However, this design is not a limitation. Alternatively, the barrel 10 and the receptacle 20 can be made in one piece, or, the receptacle 20 and the front cap 30 can be made in one piece, or, the front cap 30 and the barrel 10 can be made in one piece, or, the barrel 10, the receptacle 20 and the front cap 30 can be made in one piece.

Alternatively, the receptacle 20 can be configured to provide only one said second through hole 22. Further, this second through holes 22 can be selectively formed in the barrel 10 or the front cap 30.

Alternatively, the filter device 4 can be simplified without including the carrier 40, or, the carrier 40 and the filter element 50 can be made in one piece.

Alternatively, instead of mounting the receptacle 20 in the barrel 10, the receptacle 20 can be mounted in the front cap 30.

The aforesaid examples and/or technical features can be separately employed or selectively combined gathered to achieve the objects of the present invention.

In conclusion, the fluid withdrawing, expelling and filtering apparatus of the present invention facilitates rapid and convenient operation, and allows reciprocation in a stable manner without biasing, achieving excellent filtration after passing of the sampled fluid through the filter element.

What is claimed is:

1. A fluid withdrawing, expelling and filtering apparatus, comprising:
   a fluid container comprising a first chamber, a second chamber, and, a first through hole and a second through hole respectively disposed in communication between said first chamber and said second chamber;
   a filter device movably disposed between a first position where said filter device opens said second through hole of said fluid container and a second position where said filter device closes said second through hole of said fluid container, said filter device comprising a filter element facing toward said first through hole; and
   a fluid withdrawing and expelling operator withdrawing and expelling a fluid through said first chamber of said fluid container,
   wherein said first through hole is disposed relatively closer to said fluid withdrawing and expelling operator than said second through hole,
   wherein said first through hole is located in the center of said fluid container,
   wherein said second through hole is located in the periphery of said fluid container,
   wherein said fluid container comprises a receptacle; said first through hole and said second through hole are located in said receptacle,
   wherein a first stop portion is located in said receptacle of said fluid container,
   wherein the receptacle is provided with a slidably-fitting inner periphery and the filter device is provided with a slidably-fitting outer periphery slidably fitted with the slidably-fitting inner periphery of the receptacle.

2. The fluid withdrawing, expelling and filtering apparatus as claimed in claim 1, wherein said fluid container comprises a front cap, and a second stop portion located in said front cap.

3. The fluid withdrawing, expelling and filtering apparatus as claimed in claim 1, wherein said fluid container comprises a barrel, and said receptacle mounted in said barrel.

4. The fluid withdrawing, expelling and filtering apparatus as claimed in claim 1, wherein said fluid container comprises a barrel, and a front cap mounted in said barrel.

* * * * *